United States Patent [19]
Heafield et al.

[11] Patent Number: 5,879,705
[45] Date of Patent: Mar. 9, 1999

[54] SUSTAINED RELEASE COMPOSITIONS OF MORPHINE AND A METHOD OF PREPARING PHARMACEUTICAL COMPOSITIONS

[75] Inventors: Joanne Heafield, Fenstanton; Trevor John Knott, Bishop's Stortford; Stewart Thomas Leslie, Cambridge; Sandra Therese Antoinette Malkowska, Ely, all of England; Ronald Brown Miller, Basel, Switzerland; Derek Allan Prater, Milton; Kevin John Smith, Histon, both of England

[73] Assignee: Euro-Celtique S.A., Luxembourg, Luxembourg

[21] Appl. No.: 843,571

[22] Filed: Apr. 18, 1997

Related U.S. Application Data

[63] Continuation of Ser. No. 269,208, Jun. 30, 1994, abandoned.

[30] Foreign Application Priority Data

| Jul. 27, 1993 | [GB] | United Kingdom | 9315467 |
| Nov. 23, 1993 | [GB] | United Kingdom | 9324045 |
| Mar. 1, 1994 | [GB] | United Kingdom | 9403922 |
| Mar. 14, 1994 | [GB] | United Kingdom | 9404928 |

[51] Int. Cl.$^6$ .................................................. A61K 9/20
[52] U.S. Cl. .......................... 424/464; 424/451; 424/484; 424/486; 424/488
[58] Field of Search ................................... 424/464, 451, 424/484, 486, 488

[56] References Cited

U.S. PATENT DOCUMENTS

| 2,738,303 | 3/1956 | Blythe | 167/82 |
| 3,634,584 | 1/1972 | Poole | 424/21 |
| 3,845,770 | 11/1974 | Theeuwes et al. | 128/260 |
| 3,870,790 | 3/1975 | Lowey et al. | 424/19 |

(List continued on next page.)

FOREIGN PATENT DOCUMENTS

| 9047732 | 7/1990 | Australia . |
| 9341654 | 2/1995 | Australia . |
| 2082573 | 11/1992 | Canada . |
| 2131350 | 1/1994 | Canada | A61K 31/135 |

(List continued on next page.)

OTHER PUBLICATIONS

El-Shanawany, S., "Sustained Release of Nitrofurantoin From Inert Wax Matrixes", J. Controlled Release vol. 26, No. 1 Issued 1993, pp. 11–19.

Kinget, Renaat and Roger Kenzel "Preparation and Properties of Granulates Containing Solid Dispersion" Acta Pharmaceutica Technologica 31 (2) 1985, pp. 57–62.

Gourlay, et al., "Influence of a high–fat meal on the absorption of morphine from oral solutions", *Clin Pharmacol Ther*, pp. 403–468, Oct. 1989.

(List continued on next page.)

*Primary Examiner*—D. Gabrielle Brouillette
*Attorney, Agent, or Firm*—Davidson, Davidson & Kappel, LLC

[57] ABSTRACT

Sustained release pharmaceutical formulations containing morphine, or a pharmaceutically acceptable salt thereof, as active ingredient, suitable for administration on a once daily basis, are disclosed. In a first aspect, an orally administrable sustained release unit dosage form gives a peak plasma level at 1.0 to 6 hours after administration. In a second aspect, the formulation provides a $W_{50}$ for the M-6-G metabolite for morphine of between 4 and 12 hours. A third aspect concerns the pharmaceutical unit dosage form obtained by compressing multiparticulates comprising a pharmaceutically active substance in a matrix of hydrophobic fusible material having a melting point of from 35° to 150° C.

11 Claims, 7 Drawing Sheets

U.S. PATENT DOCUMENTS

| | | | |
|---|---|---|---|
| 3,916,889 | 11/1975 | Russell | 128/145.8 |
| 3,916,899 | 11/1975 | Theeuwes et al. | 128/145.8 |
| 4,063,064 | 12/1977 | Saunders et al. | 219/121 |
| 4,088,864 | 5/1978 | Theeuwes et al. | 219/121 LM |
| 4,132,753 | 1/1979 | Blichare et al. | 264/75 |
| 4,310,483 | 1/1982 | Dorfel et al. | 264/117 |
| 4,377,568 | 3/1983 | Chopra | 424/31 |
| 4,385,078 | 5/1983 | Onda et al. | 424/3 |
| 4,389,393 | 10/1985 | Schor et al. | 424/19 |
| 4,421,736 | 12/1993 | Walters | 424/19 |
| 4,443,428 | 4/1984 | Oshlack | 424/22 |
| 4,483,847 | 11/1984 | Augart | 424/470 |
| 4,520,172 | 5/1985 | Lehmann et al. | 525/369 |
| 4,548,990 | 10/1985 | Mueller et al. | 525/123 |
| 4,557,925 | 12/1985 | Lindahl et al. | 424/19 |
| 4,600,645 | 7/1986 | Ghebre-Sellassie et al. | 428/403 |
| 4,708,874 | 11/1987 | De Haan et al. | 424/470 |
| 4,728,513 | 3/1988 | Ventouras | 424/461 |
| 4,797,410 | 1/1989 | El-Fakahany | 514/356 |
| 4,806,337 | 2/1989 | Snipes et al. | 71/65 |
| 4,828,836 | 5/1989 | Elger et al. | 424/419 |
| 4,834,984 | 5/1989 | Goldie et al. | 424/488 |
| 4,834,985 | 5/1989 | Elger et al. | 424/488 |
| 4,844,907 | 7/1989 | Elger et al. | 424/465 |
| 4,844,909 | 7/1989 | Goldie et al. | 424/480 |
| 4,861,598 | 8/1989 | Oshlack | 424/468 |
| 4,894,234 | 1/1990 | Sharma et al. | 424/440 |
| 4,935,246 | 6/1990 | Ahrens | 424/490 |
| 4,967,486 | 11/1990 | Doelling | 34/1 |
| 4,970,075 | 11/1990 | Oshlack | 424/451 |
| 4,983,730 | 1/1991 | Domeshek et al. | 536/69 |
| 4,990,341 | 2/1991 | Goldie et al. | 424/484 |
| 5,007,790 | 4/1991 | Shell | 424/451 |
| 5,023,089 | 6/1991 | Sakamoto et al. | 424/502 |
| 5,024,842 | 6/1991 | Edgren et al. | 424/473 |
| 5,026,560 | 6/1991 | Makino et al. | 424/494 |
| 5,030,400 | 7/1991 | Danielsen et al. | 264/101 |
| 5,071,646 | 12/1991 | Malkowska et al. | 424/497 |
| 5,122,384 | 6/1992 | Paradissis et al. | 424/451 |
| 5,126,145 | 6/1992 | Evenstad et al. | 424/465 |
| 5,132,142 | 7/1992 | Jones et al. | 427/196 |
| 5,133,974 | 7/1992 | Paradissis et al. | 424/480 |
| 5,167,964 | 12/1992 | Muhammed et al. | 424/482 |
| 5,169,645 | 12/1992 | Shukla et al. | 424/499 |
| 5,178,868 | 1/1993 | Malmquist et al. | 424/490 |
| 5,196,203 | 3/1993 | Boehm | 424/469 |
| 5,202,128 | 4/1993 | Morella | 424/469 |
| 5,266,331 | 11/1993 | Oshlack et al. | 424/468 |
| 5,273,760 | 12/1993 | Oshlack et al. | 424/480 |
| 5,283,065 | 2/1994 | Doyon et al. | 424/467 |
| 5,286,493 | 2/1994 | Oshlack et al. | 424/468 |
| 5,292,461 | 3/1994 | Juch et al. | 264/37 |
| 5,321,012 | 6/1994 | Mayer et al. | 514/25 |
| 5,330,766 | 7/1994 | Morella et al. | 424/490 |
| 5,378,474 | 1/1995 | Morella et al. | 424/469 |
| 5,403,593 | 4/1995 | Royce | 424/489 |
| 5,411,745 | 5/1995 | Oshlack et al. | 424/456 |
| 5,453,283 | 9/1995 | Munch et al. | 424/489 |
| 5,456,923 | 10/1995 | Nakamichi et al. | 424/489 |
| 5,460,826 | 10/1995 | Merrill et al. | 424/470 |
| 5,472,712 | 12/1995 | Oshlack et al. | 424/480 |
| 5,500,227 | 3/1996 | Oshlack et al. | 424/476 |
| 5,508,042 | 4/1996 | Oshlack et al. | 424/468 |
| 5,520,931 | 5/1996 | Perrson | 424/473 |
| 5,549,912 | 8/1996 | Oshlack et al. | 424/468 |
| 5,580,578 | 12/1996 | Oshlack et al. | 424/468 |
| 5,601,842 | 2/1997 | Bartholomaeus | 424/464 |
| 5,614,218 | 3/1997 | Olsson | 424/456 |
| 5,629,011 | 5/1997 | Illum | 424/434 |
| 5,672,360 | 9/1997 | Sackler | 424/490 |

FOREIGN PATENT DOCUMENTS

| | | | |
|---|---|---|---|
| 0097523 | 1/1984 | European Pat. Off. | A61K 9/26 |
| 0108218 | 5/1984 | European Pat. Off. | A61K 9/22 |
| 0147780 | 7/1985 | European Pat. Off. | A61K 9/32 |
| 0235986 | 9/1987 | European Pat. Off. | A61K 9/16 |
| 0253104 | 1/1988 | European Pat. Off. | A61K 9/00 |
| 0271193 | 6/1988 | European Pat. Off. | A61K 31/485 |
| 03272985 | 1/1989 | European Pat. Off. | A61K 9/52 |
| 0361910 | 4/1990 | European Pat. Off. | A61K 9/16 |
| 0377517 | 7/1990 | European Pat. Off. | A61K 31/52 |
| 0377518 | 7/1990 | European Pat. Off. | A61K 9/52 |
| 0388954 | 9/1990 | European Pat. Off. | A61K 9/14 |
| 0415693 | 3/1991 | European Pat. Off. | A61K 37/02 |
| 0452145 | 10/1991 | European Pat. Off. | A61K 9/14 |
| 0533297 | 3/1993 | European Pat. Off. | A61K 9/16 |
| 0534628 | 3/1993 | European Pat. Off. | A61K 31/485 |
| 9532348 | 3/1993 | European Pat. Off. | A61K 31/135 |
| 0535841 | 4/1993 | European Pat. Off. | A61K 31/485 |
| 0546676 | 6/1993 | European Pat. Off. | A61K 31/60 |
| 0548448 | 6/1993 | European Pat. Off. | A61K 9/50 |
| 0580860 | 2/1994 | European Pat. Off. | A61K 9/14 |
| 0361680 | 7/1994 | European Pat. Off. | A61K 9/46 |
| 0609961 | 8/1994 | European Pat. Off. | A61K 31/485 |
| 0430287 | 10/1994 | European Pat. Off. | A61K 9/54 |
| 0636370 | 2/1995 | European Pat. Off. | A61K 31/485 |
| 0665010 | 8/1995 | European Pat. Off. | A61K 9/26 |
| 377518 | 2/1996 | European Pat. Off. | . |
| 2053681 | 2/1981 | United Kingdom | A61K 9/22 |
| 2178313 | 2/1987 | United Kingdom | A61K 9/14 |
| 9201446 | 2/1992 | WIPO | A61K 9/50 |
| 9202209 | 2/1992 | WIPO | A61K 9/22 |
| 9206679 | 4/1992 | WIPO | A61K 9/16 |
| 92/08459 | 5/1992 | WIPO | A61K 31/485 |
| 9304675 | 3/1993 | WIPO | A61K 31/16 |
| 9307859 | 4/1993 | WIPO | A61K 9/16 |
| WO 9307861 | 4/1993 | WIPO | A61K 9/50 |
| 9310765 | 6/1993 | WIPO | A61K 9/22 |
| 9318753 | 9/1993 | WIPO | . |
| WO 9403160 | 2/1994 | WIPO | A61K 9/32 |
| WO 9403161 | 2/1994 | WIPO | A61K 9/52 |
| WO 9405262 | 3/1994 | WIPO | A61K 9/16 |
| 9422431 | 10/1994 | WIPO | A61K 9/20 |
| 9423700 | 10/1994 | WIPO | A61K 9/16 |
| 9600066 | 1/1996 | WIPO | A61K 31/485 |
| 9601629 | 1/1996 | WIPO | A61K 31/485 |
| 9614088 | 3/1996 | WIPO | A61K 9/14 |

OTHER PUBLICATIONS

R.. West et al. World Congress on Pain Abstracts 997–1001, Aug. 26, 1993.

Advertisement: Roxanol SR., 1988 Roxane Labs, Inc.

Advertisement: Ms. Contin., 1986, 1987 The Purdue Frederick Company.

Abraham Sunshine, et al., "Analgesic or al efficacy of tramadol hydrochlorine in postoperative pain", *Clin. Pharmacol. Ther.*, Jun. 1992, pp. 740–746.

E. Beubler, "Medikamentose Schmerztherapie: Kriterien, Möglichkeiten, Risken", *Therapiewoche Österreich*, 7,2 (1992), pp. 90–96 with English Translation.

N. Yokokawa, et al., "Relationship between plasma concentration of morphine and analgesic effectiveness", *Postgrad Med J.*, (1991) 67 (Suppl. 2), pp. 550–554.

Physicians Desk Reference 1994, 48th Edition, pp. 1821–1824.

Abstracts from the Twelfth Annual Congress of the Oncology Nursing Society, May 1987.

J. Lapin et al., "Cancer Pain Management with a Controlled Release Oral Morphine Preparation", Journ. of Pain and Sympton Manag., v 4 (3), pp. 146–151, 1989.

J. Lapin et al., "Guildelines for use of Controlled Release Oral Morphine in Cancer Pain Management",Cancer Nursing, v 12 (4), pp. 202–208, 1989.

R.F. Kaiko, "The Pre–and Postoperative Use of Controlled–Release Morphine (MS Contin Tablets): A Review of the Published Literature", Medical Department, The Purdue Frederick Company, Royal Society of Medical Services, International Congress, Symposium Services, No. 149, pp. 147–160 (1989).

H.F. Slowey et al., "Effect of Premedication with Controlled–Release Oral Morphine on Postoperative Pain", Anaesthesia, 1985, vol. 40, pp. 438–440.

McTaggart, C.M., et al., "The Evaluation of Formulation and Processing Conditions of a Melt Granulation Process", Int. J. Pharm., vol. 19, No. 2, issued 1984 pp. 139–148.

Kaiko, et al. "A single–dose study of the effect of food ingestion and timing of dose administration on the pharmacokinetic profile of 30 mg sustained–release morphine sulfate tablets", *Current Therapeutic Reseach*, pp. 869–878, vol. 47, No. 5, May 1990.

Kaiko, et al. "Controlled–release morphine bioavailability (MS Contin® tablets) in the presence and absence of food" *The Hospice Journal*, pp. 17–30, vol. 6(4) 1990.

Gourlay, et al. "The reproducibility of bioavailability of oral morphine from solution under fed and fasted conditions", *Journal of Pain and Symptom Management*, pp. 431–436, vol. 6, No. 7, Oct. 1991.

R. Kaiko and T. Hunt, "Comparison of the Pharmacokinetic Profiles of Two Oral Controlled–Release Morphine Formulations in Healthy Young Adults", Clin. Thera. vol. 13, No. 4, pp. 484–488, 1991.

S. Bloomfield, et al., "Analgesic efficacy and potency of two oral controlled–release morphine preparations", Clin. Pharmacol. Ther., vol. 53, No. 4, pp. 469–478, 1993.

Flanders, P., et al., "The Control of Drug Release From Conventional Melt Granulation Matrices", *Drug Development and Industrial Pharmacy*, vol. 13, No. 6, pp. 1001–1022 (1987).

Kaiko, Robert, et al., "A single–dose study of the effect of food ingestion and timing of dose administration on the pharmacokinetic profile of 3–mg sustained release morphine sulfate tablets", *Current Therapeutic Research*, vol. 47, No. 5, pp. 869–876 (May 1990).

McTaggart, Celia M., et al., "The evaluation of formulation and processing conditions of a melt granulation process", *International Journal of Pharmaceutics*, vol. 19, pp. 139–148 (1984).

Schaefer, T., et al., "Melt granulation in a laboratory scale high shear mixer", *Drug Development and Industrial Pharmacy*, vol. 16, No. 8, pp. 1249–1277 (1990).

Thomsen, L. Juul, et al., "Prolonged Release Matrix Pellets Prepared by Melt Pelletization I. Process Variables", *Drug Development and Industrial Pharmacy*, vol. 19, No. 15, pp. 1867–1887 (1993).

Thomsen, L. Juul, et al., "Prolonged Release Matrix Pellets Prepared by Melt Pelletization II. Hydrophpbic Substances as Meltable Binders", *Drug Development and Industrial Pharmacy*, vol. 19, No. 7, pp. 1179–1197 (1994).

Thomsen, L. Juul, "Utilizing melt pelletization technique for the preparation of prolonged release products", *Pelletization*, (material elaborated by assistant prof. Lars Juul Thomsen, Department of Pharmaceutics, Royal Danish School of Pharmacy for the DIE course Pelletization Technology, Nov. 1992, 106 pages plus 3 appendices.

Thomsen, L. Juul, "Prolonged Release Matrix Pellets Prepared by Melt Pelletization. Part IV: Drug Conent, Drug Particle Size, and Binder Composition", *Pharmaceutical Technology Europa*, pp. 19–24 (Oct. 1994).

SUSTAINED RELEASE COMPOSITIONS OF MORPHINE AND A METHOD OF PREPARING PHARMACEUTICAL COMPOSITIONS

This application is a continuation application of U.S. Ser. No. 08/269,208 filed Jun. 30, 1994 (abandoned).

BACKGROUND OF THE INVENTION

This invention is concerned with improvements in and relating to sustained release compositions and, more particularly, is concerned with sustained release orally administrable dosage unit forms containing morphine, or a pharmaceutically acceptable salt thereof, as active ingredient.

The present invention also relates generally to a method of manufacturing an orally administrable dosage form, preferably sustained release granules/multiparticulates and compressed multiparticulates, such multiparticulates having diameters ranging from 0.1 to 3.0 mm; the method of the invention provides multiparticulates in an unexpectedly high yield.

Morphine is an opioid analgesic well established for use in the treatment of pain, especially moderate to severe pain. Morphine-containing compositions in sustained release form are currently commercially available as so-called "twice-a-day" formulations, that is formulations having a duration of activity of 12 hours or more and accordingly requiring to be administered twice a day.

OBJECTS AND SUMMARY OF THE INVENTION

It is one object of the present invention to provide a morphine-containing sustained release orally administrable dosage unit form which has an effective duration of activity of 24 hours or more and, hence, is suitable for administration on a once daily basis.

It has surprisingly been found, in accordance with the present invention, that effective therapeutic activity over a period of 24 hours or more may be obtained from a morphine-containing sustained release formulation which gives an in vivo peak plasma level relatively early after administration, that is from 1.0 to 6 hours after administration preferably 1 to 4 hours eg 1 to 3.5 hours.

Accordingly, one embodiment of the composition of the invention provides an orally administrable sustained release dosage unit form containing morphine, or a pharmaceutically acceptable salt thereof, as active ingredient which formulation gives a peak plasma level from 1 to 6 hours, preferably 1 to 4 hours e.g. 1 to 3.5 hours, after administration.

It has been found that in a group eg. n=5, of healthy volunteers such dosage units, when administered in a single dose in the fasted state, gave median $T_{max}$ values in the range of 1 to 4.25 hours.

When the morphine is administered as morphine sulphate and the method of plasma analysis is high performance liquid chromatography, the peak plasma level of morphine (per ml of plasma) is preferably from $0.5 \times 10^{-7}$ to $7.5 \times 10^{-7}$ times the amount of morphine sulphate orally administered. When morphine base or a salt other than the sulphate is administered, the preferred ratio of drug administered to peak plasma level should be adjusted according to the molecular weight of the base or salt.

The dosage unit form in accordance with the invention should contain sufficient morphine, or salt thereof, to give therapeutic activity over a period of at least 24 hours. The actual amount of morphine, or salt, in any particular dosage form will of course depend upon a number of variables including (i) the number of dosage forms intended to be administered at any one time and (ii) the intended dosage for any particular patient. Conveniently, however, dosage unit forms in accordance with the invention will contain from 10 to 500 mg of morphine (calculated as morphine sulphate) and thus, for example, typical dosage unit forms in accordance with the invention are those containing 20, 30, 60, 90, 120, 150 and 200 mg of morphine (calculated as above).

Morphine-6-glucuronide (hereinafter M-6-G) is a known metabolite of morphine and, itself, has powerful analgesic properties, at least comparable with those of morphine.

We have found, in accordance with another aspect of the invention, that a pharmaceutical formulation, containing an effective amount of morphine or pharmaceutically acceptable salt thereof, effective for at least 24 hourly dosing, is characterized by a $W_{50}$ for the M-6-G metabolite of between 4 and 12 hours, and preferably has a $T_{max}$ of M-6-G in the range 1 to 6.5 hours, more preferably 3 to 6.5 hours, and even more preferably 3.5 to 6 hours.

The $W_{50}$ parameter defines the width of the plasma profile at 50% $C_{max}$, i.e. the duration over which the plasma concentrations are equal to or greater than 50% of the peak concentration. The parameter is determined by linear interpolation of the observed data and represents the difference in time between the first (or only) upslope crossing and the last (or only) downslope crossing in the plasma profile.

We have observed that, surprisingly, formulations in accordance with the invention, which are characterized by a $W_{50}$ for M-6-G in the range specified, are usually also characterized by a $W_{50}$ for morphine within a similar range. Accordingly, in accordance with another, preferred, aspect of the invention a pharmaceutical formulation, containing an effective amount of morphine or pharmaceutically acceptable salt thereof, effective for at least 24 hour dosing, is characterized by a $W_{50}$ for morphine of between 4 and 12 hours, and preferably has a $T_{max}$ in the range of 1 to 6.5 hours, more preferably 1 to 4 hours e.g. 1 to 3.5 hours after administration.

A preferred formulation in accordance with this aspect of the invention is characterized by the foregoing parameters when dosed to patients in the fasted state.

Preferred values for $W_{50}$ for M-6-G and morphine are in the range of about 5.5 to 12 or 5.5 to 11 or even 6 to 10 hours.

The $C_{maxs}$ of formulations in accordance with the invention are dose dependant. For instance, a preferred embodiment containing 60 mg morphine sulphate when administered as a single dose is characterized by a $C_{max}$ for M-6-G in the range of from 65 ng/ml to 150 ng/ml. Another such preferred embodiment is characterized by a $C_{max}$ for morphine in the range of from 7.5 to 20 ng/ml.

One preferred embodiment described herein, after single dosing to 5 fasted volunteers was found to have $W_{50}$, for morphine and M-6-G in the range 5.5 to 12 hours.

It has been found that in a group e.g. n=5, of healthy volunteers one embodiment of such dosage units, when administered in a single dose in the fasted state, gave median $T_{max}$ values of M-6-G in the range of 3.5 to 6 hours, e.g. 4 to 6.0 hours and for morphine in the range of 2.5 to 5 hours.

It has further been found, in accordance with the present invention, that in order to achieve the desired time of peak plasma level of morphine and M-6-G and to provide effective activity over a period of at least 24 hours, the in vitro release characteristics of the formulation [when measured by the modified Ph. Eur. Basket method at 100 rpm in 900 ml aqueous buffer (pH 6.5) containing 0.05% w/v Polysorbate 80 at 37° C.] are preferably as set out below:

| Hours After | % Morphine (salt) released | |
|---|---|---|
| Start of Test | Suitable | Preferred |
| 2 | 5–30 | 5–20 |
| 4 | 15–50 | 15–35 |
| 6 | 20–60 | 20–45 |
| 12 | 35–75 | 40–70 |
| 18 | 45–100 | 50–80 |
| 24 | 55–100 | 60–100 |

DETAILED DESCRIPTION OF THE PREFERRED EMBODIMENT

Figure 1:
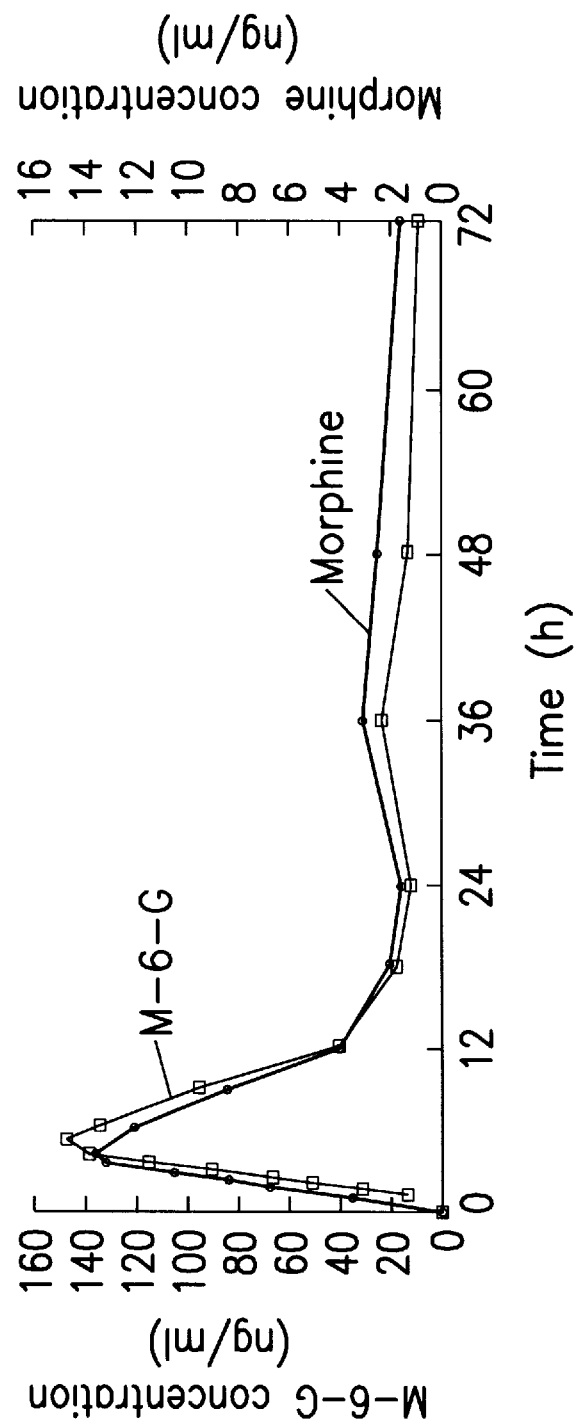
FIGS. 1 to 5 are plasma profiles of morphine and M-6-G in each of five volunteers after dosing them with a formulation in accordance with the invention.
Figure 2:
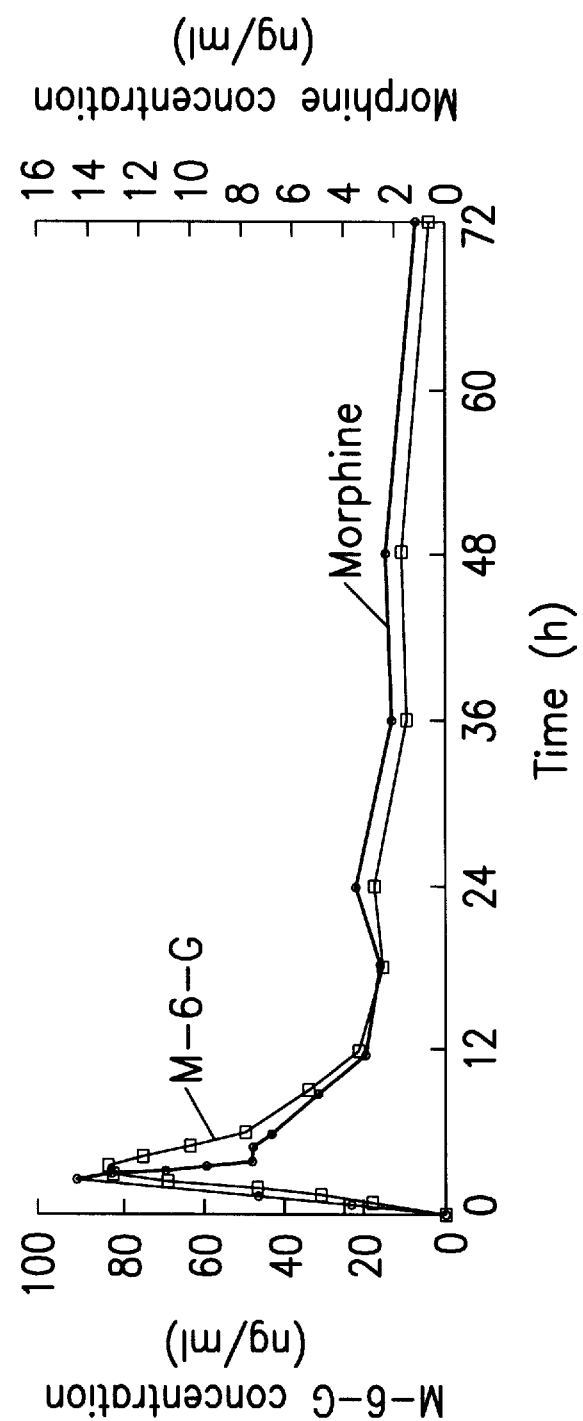
Figure 3:
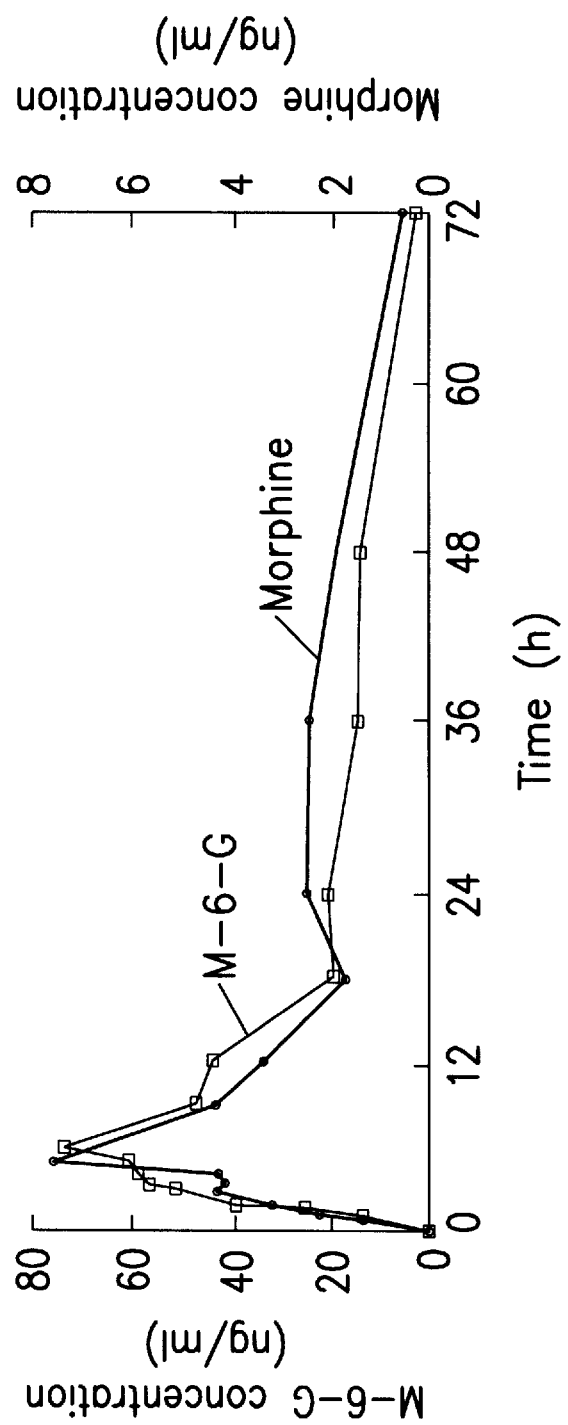
Figure 4:
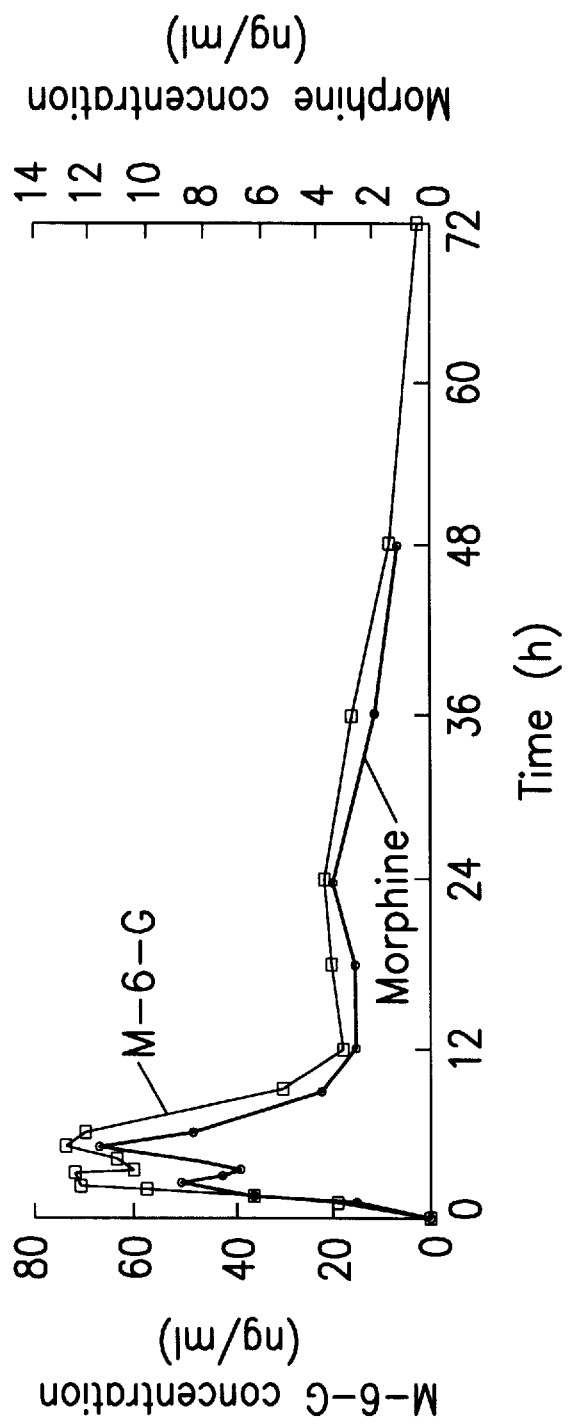
Figure 5:
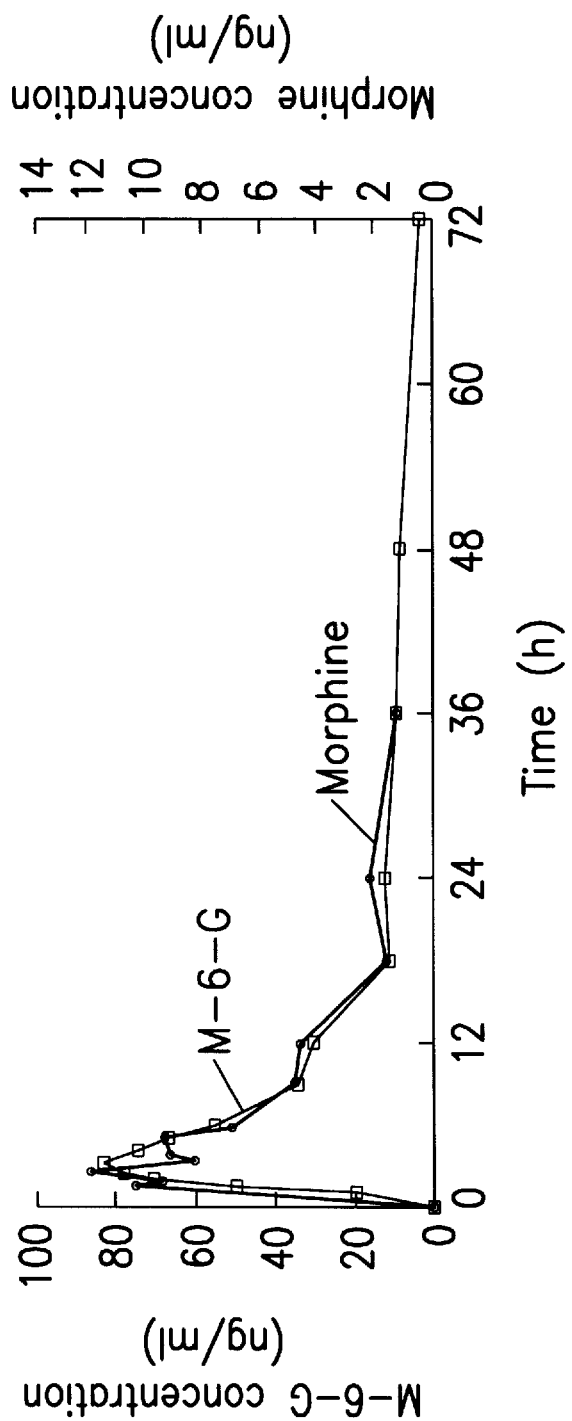

The compositions of the invention may be provided in a variety of forms, for example as tablet or capsules containing granules, spheroids or pellets. Commonly, the composition will comprise the active ingredient (morphine or salt thereof) together with a diluent which may serve to modify the release of the active ingredient. A preferred form of unit dose form in accordance with the invention comprises a capsule filled with multiparticulates essentially comprising the active ingredient, a hydrophobic fusible carrier or diluent and optionally a hydrophilic release modifier. In particular, the multiparticulates are preferably prepared by a process essentially comprising forming a mixture of dry active ingredient and fusible release control materials followed by mechanically working the mixture in a high speed mixer at a rate and energy input such that sufficient energy is supplied to the fusible material to melt or soften it whereby it forms multiparticulates with the active ingredient. The resultant multiparticulates are suitably sieved and cooled to give multiparticulates having a particle size range from 0.1 to 3.0 mm, preferably 0.25 to 2.0 mm. A preferred and novel process of this kind is described below which is suitable for the commercial production of dosage units containing morphine or other active substances.

When using such a processing technique it has been found that, in order to most readily achieve the desired release characteristics (both in vivo and in vitro as discussed above) the composition to be processed should comprise two essential ingredients namely:

(a) active ingredient (morphine or salt thereof); and (b) hydrophobic fusible carrier or diluent; optionally together with (c) a release control component comprising a water-soluble fusible material or a particulate soluble or insoluble organic or inorganic material.

We have found that the total amount of active ingredient in the composition may vary within wide limits, for example from 10 to 60% by weight thereof.

The hydrophobic fusible component (b) should be a hydrophobic material such as a natural or synthetic wax or oil, for example hydrogenated vegetable oil or hydrogenated castor oil, and suitably has a melting point of from 35° to 100° C., preferably 45° to 90° C.

The release modifying component (c), when a water soluble fusible material, is conveniently a polyethylene glycol and, when a particulate material, is conveniently a pharmaceutically acceptable material such as dicalcium phosphate or lactose.

Incorporation of lower levels of morphine, for example between 10 and 30% by weight, necessitate inclusion of low levels of a release modifying component, for example 5 to 15% by weight polyethylene glycol 6000, to achieve a satisfactory in vitro release rate. At higher drug loadings, for example 40 to 60% by weight it is particularly surprising that only incorporation of very small amounts of polyethylene glycol, for example 0.01 to 1% by weight are required to modify the in vitro release rate.

Alternatively the morphine (or salt thereof) may be formulated (e.g. by dry or wet granulation or by blending) in a controlled release mixture formed of components other than fusible components. Suitable materials for inclusion in a controlled release matrix include, for example (a) Hydrophilic or hydrophobic polymers, such as gums, cellulose ethers, protein derived materials, nylon, acrylic resins, polylactic acid, polyvinylchloride, starches, polyvinylpyrrolidones, cellulose acetate phthalate. Of these polymers, cellulose ethers especially substituted cellulose ethers such as alkylcelluloses (such as ethylcellulose), $C_1$–$C_6$ hydroxyalkylcelluloses (such as hydroxypropylcellulose and especially hydroxyethyl cellulose) and acrylic resins (for example methacrylates such as methacrylic acid copolymers) are preferred. The controlled release matrix may conveniently contain between 1% and 80% (by weight) of hydrophilic or hydrophobic polymer.

(b) Digestible, long chain ($C_8$–$C_{50}$, especially $C_8$–$C_{40}$), substituted or unsubstituted hydrocarbons, such as fatty acids, hydrogenated vegetable oils such as Cutina (Trade Mark), fatty alcohols (such as lauryl, myristyl, stearyl, cetyl or preferably cetostearyl alcohol), glyceryl esters of fatty acids for example glyceryl esters of fatty acids for example glyceryl monostearate mineral oils and waxes (such as beeswax, glycowax, castor wax or carnauba wax). Hydrocarbons having a melting point of between 25° C. and 90° C. are preferred. Of these long chain hydrocarbon materials, fatty (aliphatic) alcohols are preferred. The matrix may contain up to 60% (by weight) of at least one digestible, long chain hydrocarbon.

(c) Polyalkylene glycols. The matrix may contain up to 60% (by weight) of at least one polyalkylene glycol.

A suitable matrix comprises one or more cellulose ethers or acrylic resins, one or more $C_{12}$–$C_{36}$, preferably $C_{14}$–$C_{22}$, aliphatic alcohols and/or one or more hydrogenated vegetable oils.

A particular suitable matrix comprises one or more alkylcelluloses, one or more $C_{12}C_{36}$, (preferably $C_{14}$–$C_{22}$) aliphatic alcohols and optionally one or more polyalkylene glycols.

Preferably the matrix contains between 0.5% and 60%, especially between 1% and 50% (by weight) of the cellulose ether.

The acrylic resin is preferably a methacrylate such as methacrylic acid copolymer USNF Type A (Eudragit L, Trade Mark), Type B (Eudragit S, Trade Mark), Type C (Eudragit L 100-55, Trade Mark), Eudragit NE 30D, Eudragit E, Eudragit RL and Eudragit RS. Preferably the matrix contains between 0.5% and 60% by weight, preferably between 1% and 50% by weight of the acrylic resin.

In the absence of polyalkylene glycol, the matrix preferably contains between 1% and 40%, especially between 2% and 36% (by weight) of the aliphatic alcohol. When polyalkylene glycol is present in the oral dosage form, then the combined weight of the aliphatic alcohol and the polyalkylene glycol preferably constitutes between 2% and 40%, especially between 2 and 36% (by weight) of the matrix.

The polyalkylene glycol may be, for example, polypropylene glycol or, which is preferred, polyethylene glycol. The number average molecular weight of the at least one polyalkylene glycol is preferably between 200 and 15000 especially between 400 and 12000. The morphine-containing controlled release matrix can readily be prepared by dispersing the active ingredient in the controlled release system using conventional pharmaceutical techniques such as melt granulation, wet granulation, dry blending, dry granulation or coprecipitation.

Another form of sustained release formulation comprises spheroids obtained by spheronizing the morphine (or salt thereof) with a spheronizing agent such as microcrystalline cellulose.

The present invention also includes a process for the manufacture of sustained release multiparticulates containing morphine or a salt thereof which comprises (a) mechanically working in a high-speed mixer, a mixture of morphine or salt thereof in particulate form and a particulate, hydrophobic fusible carrier or diluent having a melting point from 35° to 150° C., e.g., to 100° C. and optionally a release control component comprising a water soluble fusible material, or a particulate soluble or insoluble organic or inorganic material at a speed and energy input which allows the carrier or diluent to melt or soften, whereby it forms agglomerates;

(b) breaking down the larger agglomerates to give controlled release seeds; and (c) continuing mechanically working with a further addition of low percentage of the carrier or diluent; and (d) optionally repeating step (c) and possible (b) one or more e.g. up to five times.

This process is capable of giving a high yield (over 80%) of multiparticulates in a desired size range, with a desired in vitro release rate, uniformity of release rate and in its preferred form surprisingly an early peak plasma level for a product with a 24 hour duration of activity.

The resulting multiparticulates may be sieved to eliminate any over or undersized material then formed into the desired dosage units by for example, encapsulation into hard gelatin capsules containing the required dose of the active substance.

Preferably morphine sulphate is used in an amount which results in multiparticulates containing between 10% and 60%, especially between about 45% and about 60% w/w active ingredient for a high dose product and 10 and 45% for a low dose product.

In this method of the invention all the drug is added in step (a) together with a major portion of the hydrophobic fusible release control material used. Preferably the amount of fusible release control material added in step (a) is between 25% and 45% w/w of the total amount of ingredients added in the entire manufacturing operation, more preferably between 30% and 40%.

In step (c) the amount of additional fusible release control material added is preferably between 5% and 20% w/w of the total amount of ingredients added, more preferably between 8 and 17% w/w.

Stage (a) of the process may be carried out in conventional high speed mixers with a standard stainless steel interior, e.g. a Collette Vactron 75 or equivalent mixer. The mixture is processed until a bed temperature above 40° C. is achieved and the resulting mixture acquires a cohesive granular texture, with particle sizes ranging from about 1–3 mm to fine powder in the case of non-aggregated original material. Such material, in the case of the embodiments described below, has the appearance of agglomerates which upon cooling below 40° C. have structural integrity and resistance to crushing between the fingers. At this stage the agglomerates are of an irregular size, shape and appearance.

The agglomerates are preferably allowed to cool. The temperature to which it cools is not critical and a temperature in the range room temperature to 45° C. e.g. to 37° C. may be conveniently used.

The agglomerates are broken down by any suitable means, which will comminute oversize agglomerates and produce a mixture of powder and small particles preferably with a diameter under 2 mm. It is currently preferred to carry out the classification using a Jackson Crockett granulator using a suitable sized mesh, or a Comil with an appropriate sized screen. We have found that if too small a mesh size is used in the aforementioned apparatus the agglomerates melting under the action of the beater or impeller will clog the mesh and prevent further throughput of mixture, thus reducing yield. A mesh size of 12 or greater or a 94G Comill screen have been found adequate.

The classified material is returned to the high speed mixer and processing continued. It is believed that this leads to cementation of the finer particles into multiparticulates of uniform size range.

In a preferred form of the method of the invention processing of the classified materials is continued, until the hydrophobic fusible materials used begin to soften/melt and additional hydrophobic fusible material is then added. Mixing is continued until the mixture has been transformed into multiparticulates of the desired predetermined size range.

In order to ensure uniform energy input into the ingredients in the high speed mixer it is preferred to supply at least part of the energy by means of microwave energy.

Energy may also be delivered through other means such as by a heating jacket or via the mixer impeller and chopper blades.

After the pellets have been formed they may then be sieved to remove any over or undersized material and are cooled or allowed to cool.

The resulting pellets may be used to prepare dosage units such as tablets or capsules in manners known per se.

In this process of the invention the temperature of the mixing bowl throughout the mechanical working is chosen so as to avoid excessive adhesion of the material to the walls of the bowl. We have generally found that the temperature should be neither too high nor too low with respect to the melting temperature of the material and it can be readily optimized to avoid the problems mentioned above. The same applies to the process of mechanically working a mixture of drug and particulate hydrophobic fusible carrier in a high speed mixture first mentioned above. For example in the processes described below in the Examples a bowl temperature of approximately 60° C. has been found to be satisfactory and avoid adhesion to the bowl.

To produce tablets in accordance with the invention, multiparticulates produced as described above may be mixed or blended with the desired excipient(s), if any, using conventional procedures e.g. using a Y-Cone or bin-blender and the resulting mixture compressed according to conventional tabletting procedure using a suitably sized tabletting tooling. Tablets can be produced using conventional tabletting machines, and in the embodiments described below were produced on a standard single punch F3 Manesty machine or Kilian RLE15 rotary tablet machine.

In order that the invention may be well understood the following examples are given by way of illustration only.

EXAMPLES 1 TO 8

Pellets, having the formulations given in Table I below, were prepared by the steps of:

(i) placing the ingredients, in a total amount by weight of 10 kg, in the bowl of a 75 liter capacity Collette Vactron Mixer (or equivalent), equipped with variable speed mixing and granulating blades;

(ii) mixing the ingredients while applying heat until the contents of the bowl are pelletized;

(iii) discharging the pellets from the mixer and sieving them to separate out the pellets collected between 0.5 and 2 mm aperture sieves.

TABLE I

| EXAMPLE NO. | 1 | 2 | 3 | 4 | 5 | 6 | 7 | 8 |
|---|---|---|---|---|---|---|---|---|
| Morphine Sulfate (wt %) | 15 | 15 | 15 | 23 | 55 | 55 | 55 | 55 |
| Hydrogenated castor oil U.S.N.F. (wt %) | 77 | 76 | 75 | 70 | — | — | — | — |
| Hydrogenated vegetable oil U.S.N.F. (wt %) | — | — | — | — | 42.8 | 45 | 44.95 | 42.0 |
| polyethylene glycol 6000 U.S.N.F. (wt %) | 8 | 9 | 10 | 7 | 0.2 | — | 0.05 | — |
| Dicalcium phosphate anhydrous USP (wt %) | — | — | — | — | 2 | — | — | 3 |

The in vitro release rates of the products of Examples 1, 2. 3 and 5 were assessed by the modified Ph. Eur. Basket method at 100 rpm in 900 ml aqueous buffer (pH 6.5) at 37° C. For each of the products, six samples of the pellets, each sample containing a total of 30 mg of morphine sulphate, were tested. The results set out in Table II below give the mean values for each of the six samples tested.

TABLE II

| | PRODUCT OF EXAMPLE | | | |
|---|---|---|---|---|
| Hours After Start of Test | 1 | 2 | 3 | 4 |
| | (% morphine released) | | | |
| 2 | 19 | 25 | 33 | 44 |
| 4 | 27 | 36 | 49 | 57 |
| 6 | 34 | 45 | 62 | 66 |
| 8 | 41 | 52 | 72 | 72 |
| 12 | 53 | 64 | 86 | 81 |
| 18 | 66 | 77 | 96 | 89 |
| 24 | 76 | 86 | 101 | 92 |

Pharmacokinetic studies in healthy human volunteers have indicated peak plasma levels of from 2.2 to 21.6 ng/ml of morphine at median times between 1.0 and 3.5 hours following administration of a single capsule containing pellets of Examples 1, 2, 3 or 5 in an amount sufficient to provide a morphine sulphate dose of 30 mg.

EXAMPLES 9 TO 12

Particles, having the formulations given in Table III below, were prepared by the steps of:

i) Placing the ingredients (a) to (c) (total batch weight 20 kg) in the bowl of a 75 liter capacity Collette Vactron Mixer (or equivalent) equipped with variable speed mixing and granulating blades;

ii) Mixing the ingredients at about 150–350 rpm while applying heat until the contents of the bowl are agglomerated.

iii) Classifying the agglomerated material by passage through a Comill and/or Jackson Crockett to obtain controlled release seeds.

iv) Warming and mixing the classified material in the bowl of a 75 liter Collette Vactron, with addition of ingredient (d), until uniform particles of the desired predetermined size range are formed in a yield of greater than 80%. This takes approximately 15 minutes.

v) Discharging the particles from the mixer and sieving them to separate out the particles collected between 0.5 and 2 mm aperture sieves.

TABLE III

| EXAMPLE | 9 | 10 | 11 |
|---|---|---|---|
| a) Morphine Sulphate (Wt %) | 55.0 | 52.19 | 53.48 |
| b) Hydrogenated Vegetable Oil USNF (Wt %) | 34.95 | 33.17 | 33.98 |
| c) Polyethylene Glycol 6000 USNF (Wt %) | 0.05 | 0.047 | 0.049 |
| d) Hydrogenated Vegetable Oil USNF (Wt %) | 10.0 | 14.60 | 12.49 |
| Yield % | 90.5 | 83.4 | 90.1 |

The in vitro release rates of Examples 9, 10 and 11 as well as Example 12 below were assessed by modified Ph. Eur. Basket method at 100 rpm in 900 ml aqueous buffer (pH 6.5) containing 0.05% w/v polysorbate 80 at 37° C. For each of the products, six samples of the particles, each sample containing a total of 60 mg of morphine sulphate were tested. The results set out in Table IV below give the mean values for each of the six samples tested.

TABLE IV

| | PRODUCT OF EXAMPLE | | |
|---|---|---|---|
| Hours After Start of Test | 9 | 10 | 11 |
| | (% morphine released) | | |
| 2 | 21 | 15 | 20 |
| 4 | 33 | 25 | 36 |
| 6 | 43 | 35 | 49 |
| 8 | 52 | 43 | 59 |
| 12 | 62 | 57 | 72 |
| 18 | 74 | 71 | 82 |
| 24 | 82 | 81 | 86 |
| 30 | 83 | 85 | 89 |

The procedure of Example 11 was repeated but the operation varied by adding the classified particles to a cold bowl of the Collette Vactron, followed by adding ingredient (d) and mixing, heating by jacket heating and microwave being applied during mixing. The in vivo release rate is given in Table IVa and demonstrates that although the composition of the products in Examples 11 and 12 are the same the different processing results in modified release rates.

TABLE IVa

PRODUCT OF EXAMPLE

| Hours After Start of Test | % of Morphine Released |
|---|---|
| 2 | 15 |
| 4 | 24 |
| 6 | 30 |
| 8 | 36 |
| 12 | 46 |
| 18 | 57 |
| 24 | 65 |
| 30 | 71 |

Particles produced according to Examples 9 to 12 were each blended with purified talc and magnesium stearate and used to fill hard gelatin capsules such that each capsule contains 60 mg of morphine sulphate. The capsules produced were used in open, randomized crossover pharmacokinetic studies. As part of these studies patients received after overnight fasting either one capsule according to the invention or one MST CONTINUS® tablet 30 mg (a twice a day preparation). Fluid intake was unrestricted from 4 hours after dosing. A low-fat lunch was provided four hours after dosing, a dinner at 10 hours post dose and a snack at 13.5 hours post-dose. No other food was allowed until a 24 hour post-dose blood sample had been withdrawn. Blood samples were taken at the following times 1, 1.5, 2, 2.5, 3, 3.5, 4, 5, 6, 9, 12, 18, 24, 36, 48 and 72 hours post-dose.

The pharmacokinetic studies using these capsules gave peak plasma levels of from 3.2 to 29.2 ng/ml of morphine at median times between 2 and 6 hours following administration and blood sampling according to the above protocol.

The capsules containing particles produced according to Examples 10 and 12 in particular gave a mean $C_{max}$ of 11.9 ng/ml at median $T_{max}$ 4 hours and mean $C_{max}$ of 9.2 ng/ml at median $T_{max}$ 2.5 hours respectively (these values represent the mean of the individual $C_{max}$ and $T_{max}$ values). In contrast the $C_{max}$ and $T_{max}$ for the patients who received MST CONTINUS® tablets were 10.6–11.4 ng/ml and 2.0–2.5 hours respectively. It was found, however, that the plasma concentrations of morphine in the blood of patients given capsules according to the invention at 24 hours were greater than the concentrations at 12 hours in those patients given MST CONTINUS® tablets.

The pharmacokinetic studies based on the particles produced in Example 9, and directed to morphine and morphine-6-glucuronide following administration of a capsule containing 60 mg of morphine sulphate in five volunteers in the fasted state gave the results shown in Table V and FIGS. 1 to 6.

TABLE V

| Volunteer | M-6-G $C_{max}$ (ng/ml) | M-6-G $T_{max}$ (h) | $W_{50}$ (h) M-6-G | $W_{50}$ (h) Morphine |
|---|---|---|---|---|
| 1 | 147.7 | 5.0 | 7.54 | 8.18 |
| 2 | 83.8 | 3.5 | 5.69 | 4.24 |
| 3 | 73.4 | 6.0 | 11.97 | 8.45 |
| 4 | 72.8 | 5.0 | 7.02 | 5.99 |
| 5 | 82.5 | 3.5 | 6.75 | 6.67 |
| Mean | 92.0 | — | 7.79 | 6.71 |
| sd | 31.5 | — | 2.43 | 1.72 |
| Median | — | 5.0 | — | — |

TABLE V-continued

| Volunteer | M-6-G $C_{max}$ (ng/ml) | M-6-G $T_{max}$ (h) | $W_{50}$ (h) M-6-G | $W_{50}$ (h) Morphine |
|---|---|---|---|---|
| Minimum | 72.8 | 3.5 | 5.69 | 4.24 |
| Maximum | 147.7 | 6.0 | 11.97 | 8.45 |

Figure 6:
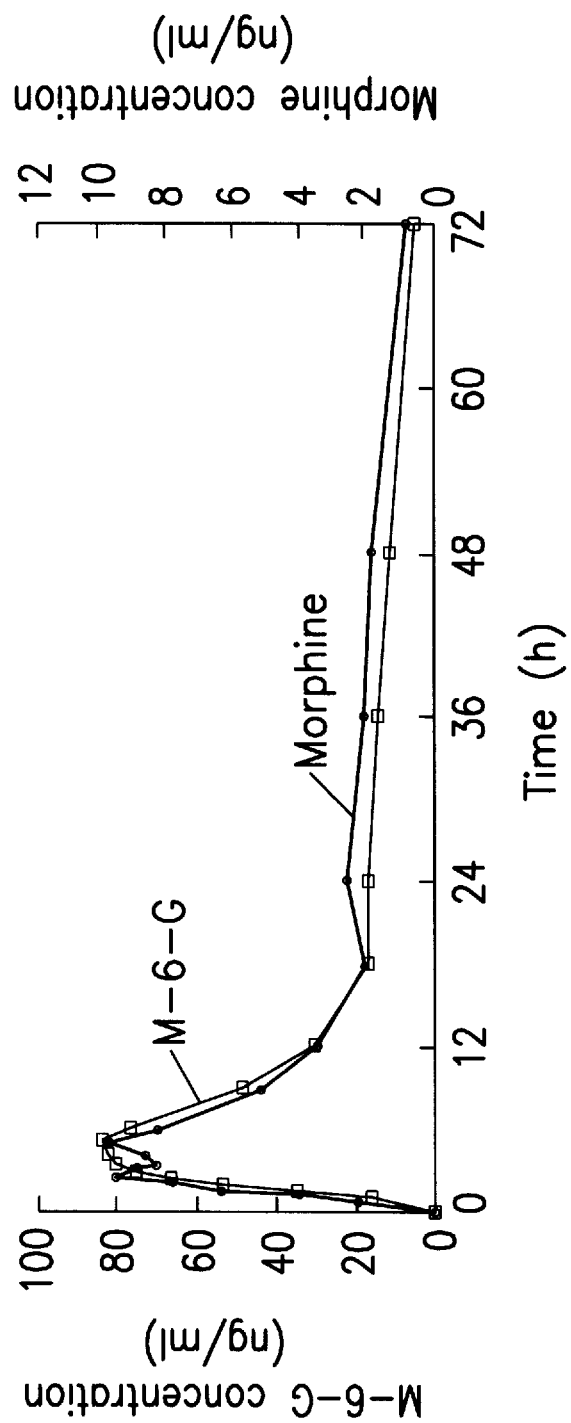
FIG. 6 shows the mean plasma profiles of morphine and M-6-G derived from the results illustrated in FIGS. 1 to 5.
Figure 7:
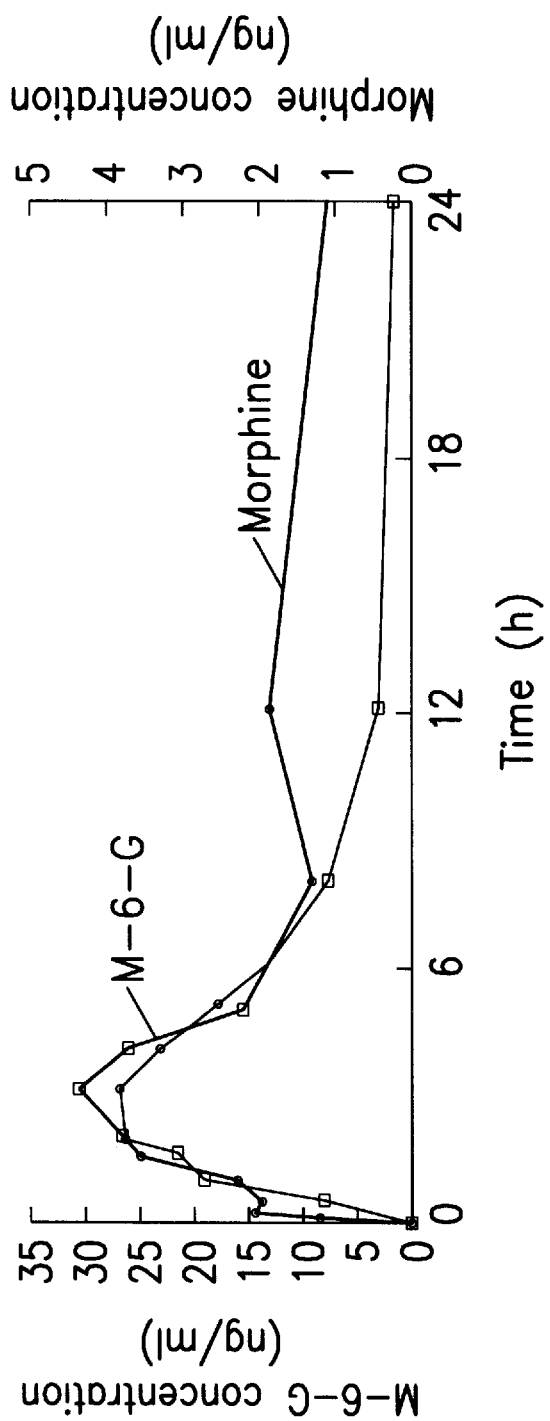
FIG. 7 shows the mean-plasma profiles of morphine and M-6-G obtained using a known controlled release morphine preparation in nine volunteers.

FIG. 7, by contrast shows the mean plasma profiles obtained after dosing nine healthy volunteers with the known bid morphine sulphate-containing preparation MST CONTINUS® under a similar test conditions, and analyzing the blood samples using a similar analytical procedure, as were used in the tests carried out with the formulations in accordance with the invention and which gave the results illustrated in Table V and FIGS. 1 to 6. it can be seen MST CONTINUS® resulted at 12 hours in mean plasma levels for M-6-G and morphine of about 14 ng/ml and 2 ng/ml respectively: the mean values for plasma levels at 24 hours obtained using the preparation in accordance with the present invention, and as illustrated in FIG. 6 were M-6-G 17.5 ng/ml and morphine 2.5 ng/ml.

EXAMPLE 13

Particles were produced analogously to Examples 9 to 12 but having the following ingredients:

| | wt % |
|---|---|
| Morphine sulphate | 55.0 |
| Hydrogenated vegetable oil | 44.7 |
| Polyethylene glycol 6000 | 0.3 |

Samples of the particles were then blended with magnesium stearate and purified talc in two lots (1 and 2) using a Y-Cone or bin-blender machine. The blended mixtures were then each compressed on a 7.1 mm diameter normal concave tooling on a single punch F3 Manestr tabletting machine. The ingredients per dosage unit amounted to the following:

TABLE VI

| | Mg/Tablet | |
|---|---|---|
| Tablet Ingredient | 1 | 2 |
| Morphine Sulphate | 60.00 | 60.00 |
| Hydrogenated Vegetable Oil | 48.77 | 48.77 |
| Polyethylene Glycol | 0.33 | 0.33 |
| Sub Total | 109.1 | 109.1 |
| Magnesium Stearate | 1.42 | 2.0 |
| Purified Talc | 2.18 | 3.0 |

The dissolution of the samples of non-compressed particles (each sample containing 60 mg of morphine sulphate) was assessed by the modified Ph. Eur Basket method described above. For the dissolution of the tablets the Ph. Eur. Basket was replaced by the Ph. Eur. Paddle Method. The results are shown in Table VII below:

TABLE VII

| Hours After Start of Test | Particles | Tablet 1 | Tablet 2 |
|---|---|---|---|
| | % morphine sulphate released | | |
| 1 | 27 | 13 | 11 |
| 2 | 43 | 20 | 17 |

TABLE VII-continued

| Hours After Start of Test | Particles | Tablet 1 | Tablet 2 |
|---|---|---|---|
| | % morphine sulphate released | | |
| 4 | 63 | 29 | 26 |
| 8 | 82 | 42 | 37 |
| 12 | 88 | 50 | 44 |
| 16 | 91 | 57 | NR* |
| 24 | 93 | 65 | NR* |
| 30 | 94 | 70 | NR* |
| 36 | 95 | 74 | NR* |

*NR = Not recorded

The above results show that the tabletting procedure results in a considerable reduction in the release rate of the active ingredient.

EXAMPLE 14

The procedure of Example 13 was repeated but with the following variations.

The particles were made with the following ingredients.

| | wt % |
|---|---|
| Morphine Sulphate | 55.0 |
| Hydrogenated Vegetable Oil | 44.4 |
| Polyethylene Glycol 6000 | 0.6 |

Two lots of tablets (3 and 4) were produced from the particles using a 7.1 mm diameter concave tooling. The ingredients per dosage unit were as follows;

TABLE VIII

| | Mg/Tablet | |
|---|---|---|
| Tablet Ingredient | 3 | 4 |
| Morphine Sulphate | 60.00 | 60.00 |
| Hydrogenated Vegetable Oil | 48.44 | 48.44 |
| Polyethylene Glycol 6000 | 0.655 | 0.655 |
| Sub Total | 109.1 | 109.1 |
| Poloxamer 188 | — | 5.0 |
| Magnesium Stearate | 2.0 | 2.0 |
| Purified Talc | 3.0 | 3.0 |

The dissolution of the tablets and samples of non-compressed particles (each sample containing 60 mg of morphine sulphate) were assessed by the methods described above. The results are shown in Table IX below:

TABLE IX

| Hours After Start of Test | Particles | Tablet 3 | Tablet 4 |
|---|---|---|---|
| | % morphine sulphate released | | |
| 1 | 56 | 16 | 19 |
| 2 | 75 | 24 | 28 |
| 4 | 90 | 34 | 38 |
| 8 | 95 | 46 | 52 |
| 12 | 97 | 54 | 60 |
| 16 | NR* | NR* | 67 |
| 24 | NR* | NR* | 77 |

*NR = Not recorded

These results demonstrate again a dramatic reduction in the release rate of the morphine sulphate resulting from compression tabletting of the particles; comparison of the release rates for Tablets 3 and 4 also show that the release rate can be adjusted by use of a surface active agent (in this case Poloxamer 188™) as a tabletting excipient, the release rate for tablet 4 which contains the surface active agents being greater than that for tablet 3 without the surface active agent.

We claim:

1. An oral sustained release pharmaceutical unit dosage form containing a therapeutically effective amount of morphine or a pharmaceutically acceptable salt thereof, the unit dosage form comprising a tablet formed from, or a capsule containing granules, spheroids or pellets, and containing an amount from about 10 mg to about 500 mg of morphine or a pharmaceutically acceptable salt thereof, said amount calculated as morphine sulfate, the granules, spheroids or pellets comprising a matrix of a natural or synthetic wax or oil with a melting point of from about 35° C. to about 100° C. and 10% to 60% by weight of morphine or pharmaceutically acceptable salt thereof, such that the unit dosage form provides a time to peak plasma level of morphine in about 1.0 to about 6.0 hours after administration, and provides morphine plasma levels which are effective for 24 hourly dosing, characterized by a width of the plasma profile at 50% $C_{max}$ ($W_{50}$) for the morphine-6-glucoronide metabolite of morphine of between 4 and 12 hours, said granules, spheroids or pellets being prepared by mixing together said morphine or salt thereof and said natural or synthetic wax or oil at a rate and energy input sufficient to cause said natural or synthetic wax or oil to melt or soften whereby it forms said granules, spheroids or pellets containing said morphine or salt thereof.

2. An oral sustained release pharmaceutical unit dosage form containing a therapeutically effective amount of morphine or a pharmaceutically acceptable salt thereof, the unit dosage form comprising a tablet formed from, or a capsule containing, granules, spheroids or pellets, and containing an amount from about 10 mg to about 500 mg of morphine or a pharmaceutically acceptable salt thereof, said amount calculated as morphine sulfate, the granules, spheroids or pellets comprising a matrix of a natural or synthetic wax or oil with a melting point of from about 35° C. to about 100° C. and 10% to 60% by weight of morphine or pharmaceutically acceptable salt thereof, said unit dosage form having in vitro release characteristics such that the formulation, when assessed by the modified European Pharmacopeia Basket Method at 100 rpm in 900 ml aqueous buffer at pH 6.5 containing 0.5% polysorbate at 37° C., releases from 5 to 30% of morphine two hours after start of test, 15 to 50% at 4 hours after start of test; 20% to 60% at 6 hours after start of test; 35 to 75% at 12 hours after start of test, from 45 to 100% at 18 hours after start of test and 55 and 100% at 24 hours after start of test such that the unit dosage form provides a time to peak plasma level of morphine in about 1.0 to about 6.0 hours after administration, and provides morphine plasma levels effective for 24 hourly dosing, characterized by a width of the plasma profile at 50% $C_{max}$ ($W_{50}$) for the morphine-6-glucoronide metabolite of morphine of between 4 and 12 hours, wherein said granules, spheroids or pellets are prepared by a process comprising the steps of a) mixing together a particulate form of said morphine or pharmaceutically acceptable salt thereof, a particulate form of said natural or synthetic wax or oil, and optionally a release control component comprising a material selected from the group consisting of a water soluble fusible material, a particulate soluble organic material, a particulate insoluble organic material, a particulate inorganic soluble material, a particulate inorganic insoluble material and mixtures thereof, at a speed and energy input which allows the carrier to melt or soften whereby it forms agglomerates; and (b) breaking down the agglomerates to give said granules, spheroids or pellets.

3. The sustained release dosage form of claim 2 wherein said dosage form further comprises a pharmaceutically acceptable inert diluent.

4. An oral sustained release pharmaceutical unit dosage form prepared by a process comprising the steps of compressing granules, spheroids or pellets comprising morphine or a salt thereof dispersed in a matrix comprising a natural or synthetic wax or oil having a melting point from 35° to 100° C., wherein said dosage form is characterized by a width of the plasma profile at 50% $C_{max}$ ($W_{50}$) for the morphine-6-glucoronide metabolite of morphine of between 4 and 12 hours.

5. The unit dosage form of claim 4, wherein said granules, spheroids or pellets are prepared by a process comprising the steps of mixing together a particulate form of said morphine or salt thereof and a particulate form of said natural or synthetic wax or oil at speed and energy input sufficient to melt or soften said hydrophobic material and to form said granules, spheroids or pellets.

6. The unit dosage form of claim 4, wherein said granules, spheroids or pellets are obtained by a process comprising the steps of mixing together said morphine or salt thereof and said natural or synthetic wax or oil at a rate and energy input sufficient to cause the natural or synthetic wax or oil to melt or soften whereby it forms said granules, spheroids or pellets and thereafter separating said granules, spheroids or pellets having a size range from about 0.1 mm to about 3 mm.

7. An orally administrable sustained release once-a-day unit dosage form comprising a plurality of granules, spheroids or pellets comprising morphine or a pharmaceutically acceptable salt thereof and a natural or synthetic wax or oil, said composition characterized by a width of the plasma profile at 50% $C_{max}$ ($W_{50}$) for said morphine of between 4 and 12 hours after administration and providing sufficient analgesia for about 24 hours after administration of said unit dosage form to a human patient.

8. The unit dosage form of claim 7, wherein said granules, spheroids or pellets are prepared by a process comprising the steps of mixing together said morphine or salt thereof and said natural or synthetic wax or oil at a rate and energy input sufficient to cause said natural or synthetic wax or oil to melt or soften whereby it forms said granules, spheroids or pellets containing said morphine and thereafter separating said granules, spheroids or pellets having a size range from about 0.1 mm to about 3 mm.

9. The unit dosage form as claimed in claim 1 which provides a time to peak plasma level of morphine in about 1.0 to about 3.5 hours after administration.

10. The unit dosage form as claimed in claim 2 which provides a time to peak plasma level of morphine in about 1.0 to about 3.5 hours after administration.

11. The unit dosage form of claim 6, wherein the mixing step incudes mixing together the morphine or salt thereof, the natural or synthetic wax or oil, and a release modifier.

* * * * *